US00PP18423P2

(12) United States Plant Patent
Verwer

(10) Patent No.: US PP18,423 P2
(45) Date of Patent: Jan. 15, 2008

(54) *DAHLIA* PLANT NAMED 'MELODY HARMONY'

(50) Latin Name: *Dahlia hybrida*
Varietal Denomination: Melody Harmony

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 11/524,415

(22) Filed: Sep. 20, 2006

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
(74) *Attorney, Agent, or Firm*—C. A. Whealy

(57) ABSTRACT

A new and distinct cultivar of *Dahlia* plant named 'Melody Harmony', characterized by its upright, somewhat outwardly spreading and mounded plant habit; freely branching growth habit; dark-colored foliage; freely flowering habit; decorative-type inflorescence form; large inflorescences with light purple-colored ray florets; and good postproduction longevity and garden performance.

1 Drawing Sheet

Botanical designation: *Dahlia hybrida.*
Cultivar denomination: 'Melody Harmony'.

BACKGROUND OF THE INVENTION

The present invention relates to a new and distinct cultivar of *Dahlia* plant, botanically known as *Dahlia hybrida,* and hereinafter referred to by the name 'Melody Harmony'.

The new *Dahlia* is a product of a planned breeding program conducted by the Inventor in Lisse, The Netherlands. The objective of the breeding program is to create new compact container-type *Dahlia* cultivars that have a freely branching growth habit, early and freely flowering habit, daisy inflorescence form, attractive ray floret coloration, and good postproduction longevity and garden performance.

The new *Dahlia* originated from a cross-pollination in Lisse, The Netherlands in 2000, of a proprietary selection of *Dahlia hybrida* identified as code number VP 61, not patented, as the female, or seed, parent with the *Dahlia hybrida* cultivar Silver Years, not patented, as the male, or pollen, parent. The new *Dahlia* was discovered and selected by the Inventor as a single flowering plant within the progeny of the stated cross-pollination in a controlled environment in Lisse, The Netherlands during the summer of 2001.

Asexual reproduction of the new *Dahlia* by cuttings since the spring of 2002 in a controlled environment in Lisse, The Netherlands, has shown that the unique features of this new *Dahlia* are stable and reproduced true to type in successive generations.

SUMMARY OF THE INVENTION

The cultivar Melody Harmony has not been observed under all possible environmental conditions. The phenotype may vary somewhat with variations in environment such as temperature and light intensity, without, however, any variance in genotype.

The following traits have been repeatedly observed and are determined to be the unique characteristics of 'Melody Harmony'. These characteristics in combination distinguish 'Melody Harmony' as a new and distinct cultivar of *Dahlia:*

1. Upright, somewhat outwardly spreading and mounded plant habit.
2. Freely branching growth habit.
3. Dark-colored foliage.
4. Freely flowering habit.
5. Decorative-type inflorescence form.
6. Large inflorescences with light purple-colored ray florets.
7. Good postproduction longevity and garden performance.

Compared to plants of the parents, the female selection and the cultivar Silver Years, plants of the new *Dahlia* differ primarily in leaf coloration, ray floret coloration and plant size.

Plants of the new *Dahlia* can be compared to plants of the *Dahlia* cultivar Melody Dixie, disclosed in U.S. Plant Pat. No. 12,911. In side-by-side comparisons conducted in Lisse, The Netherlands, plants of the new *Dahlia* differed from plants of the cultivar Melody Dixie in the following characteristics:

1. Plants of the new *Dahlia* were larger than plants of the cultivar Melody Dixie.
2. Plants of the new *Dahlia* were more freely branching and bushier than plants of the cultivar Melody Dixie.
3. Plants of the new *Dahlia* and the cultivar Melody Dixie differed in leaf coloration.
4. Plants of the new *Dahlia* had larger inflorescences than plants of the cultivar Melody Dixie.
5. Ray florets of plants of the new *Dahlia* were light purple in color whereas ray florets of plants of the cultivar Melody Dixie were dark purple in color.

BRIEF DESCRIPTION OF THE PHOTOGRAPH

The accompanying photograph illustrates the overall appearance of the new *Dahlia.* The photograph shows the colors as true as it is reasonably possible to obtain in colored reproductions of this type. Colors in the photograph may differ slightly from the color values cited in the detailed botanical description which accurately describe the colors of the new *Dahlia*. The photograph comprises a side perspective view of a typical flowering plant of 'Melody Harmony' grown in a container.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lisse, The Netherlands during the summer in an outdoor nursery and under conditions and practices which approximate those generally used in commercial *Dahlia* production. During the production of the plants, day temperatures ranged from 15° C. to 30° C. and night temperatures ranged from 10° C. to 20° C. Plants were pinched one time about three to four weeks after planting. Measurements and numerical values represent averages for typical flowering plants. Plants were about four months old when the photograph and description were taken.

Botanical classification: *Dahlia hybrida* cultivar Melody Harmony.

Parentage:

*Female, or seed, parent.*—Proprietary selection of *Dahlia hybrida* identified as code number VP 61, not patented.

*Male, or pollen, parent.*—*Dahlia hybrida* cultivar Silver Years, not patented.

Propagation:

*Type.*—By cuttings.

*Time to initiate roots, summer.*—About ten days at temperatures of about 18° C.

*Time to initiate roots, winter.*—About twelve days at temperatures of about 18° C.

*Time to produce a rooted young plant, summer.*—About 24 days at temperatures of about 18° C.

*Time to produce a rooted young plant, winter.*—About 27 days at temperatures of about 18° C.

*Root description.*—Fine to fleshy; tuber development has not been observed.

*Rooting habit.*—Freely branching; dense.

Plant description:

*Plant form/growth habit.*—Upright to somewhat outwardly spreading; mounded plant form. Freely basal branching with about four lateral branches each with about three to four secondary branches. Inflorescences held above the foliage on strong peduncles; bushy and dense. Vigorous growth habit.

*Plant height.*—about 65 cm.

*Plant diameter or spread.*—About 40 cm.

*Lateral branches.*—Length: About 50 cm. Diameter: Towards the base, about 1.2 cm; towards the apex, about 3 mm. Internode length: about 2 cm to 13 cm. Aspect: Erect to somewhat outwardly spreading. Strength: Strong. Texture: Smooth, glabrous. Color: 187A.

Foliage description:

*Arrangement.*—Leaves opposite; leaves may be single or compound with three or five leaflets.

*Shape.*—Ovate.

*Apex.*—Acuminate.

*Base.*—Attenuate.

*Margin.*—Serrate and divided; sinuses divergent.

*Length.*—Single leaves: About 8 cm. Compound leaves with three leaflets: About 14 cm. Compound leaves with five leaflets: About 22 cm.

*Width.*—Single leaves: About 2 cm. Compound leaves with three leaflets: About 9 cm. Compound leaves with five leaflets: About 14 cm.

*Venation pattern.*—Pinnate.

*Texture, upper and lower surfaces.*—Smooth, glabrous.

*Color.*—Developing foliage, upper surface: 139A. Developing foliage, lower surface: Close to 148B. Fully expanded foliage, upper surface: 139A tinted heavily with between 187A and 200A; venation, 187A. Fully expanded foliage, lower surface: 148B; venation, 183A.

*Petiole length.*—Single leaves: About 5 mm. Compound leaves with three leaflets: About 2 cm. Compound leaves with five leaflets: About 6 cm.

*Petiole diameter.*—Single leaves: About 4 mm. Compound leaves with three leaflets: About 4 mm. Compound leaves with five leaflets: About 4 mm.

*Petiole texture, upper and lower surfaces.*—Smooth, glabrous.

*Petiole color, upper surface.*—187A.

*Petiole color, lower surface.*—183A.

Inflorescence description:

*Appearance.*—Rotate single inflorescence form with ray and disc florets. Inflorescences positioned above the foliage on strong peduncles. Inflorescences face upright to slightly outwardly. Freely flowering habit; about 25 inflorescences develop per plant. Inflorescences persistent. Inflorescences not fragrant.

*Time to flower.*—Plants flower continuously during the summer and autumn in The Netherlands.

*Post-production longevity.*—Inflorescences maintain good substance for about 20 days on the plant and for about five days as a cut flower.

*Inflorescence bud.*—Height: About 1.5 cm. Diameter: About 1.9 cm. Shape: Oblate. Color: 187A.

*Inflorescence size.*—Diameter: About 14 cm. Depth (height): About 5 cm. Disc diameter: About 1.6 cm. Receptacle height: About 1.1 cm. Receptacle diameter: About 2 cm.

*Ray florets.*—Length: About 4.5 cm. Width: About 2 cm. Shape: Ovate. Apex: Mucronate. Base: Attenuate. Aspect: Initially upright to roughly perpendicular to the peduncle to reflexed; mostly flat. Texture, upper and lower surfaces: Smooth, glabrous; satiny. Number of ray florets per inflorescence: About 150 arranged in about twelve whorls. Color: When opening, upper surface: 69A; mid-section, 77B. When opening, lower surface: 69C; mid-section, 72B. Fully opened, upper and lower surfaces: Between 69A and 69B; along longitudinal ribs and towards the apex, 77B. Color becoming closer to 69C with development.

*Disc florets.*—Shape: Tubular, apex dentate. Length: About 1.5 cm. Diameter, apex: About 3 mm. Diameter, base: About 1 mm. Number of disc florets per inflorescence: About ten. Color: Immature: Towards the apex, 23B; towards the base, 1C. Mature: Apex: 21A. Mid-section: 6A. Base: 1C.

*Phyllaries.*—Quantity per inflorescence: About eight arranged in a single whorl. Length: About 1.4 cm. Width: About 1 cm. Shape: Ovate. Apex: Acute.

Base: Attenuate. Margin: Entire. Texture, upper and lower surfaces: Smooth, glabrous; satiny. Color, upper surface: 138A tinted with 183A. Color, lower surface: 137A.

*Peduncles.*—Length: Terminal peduncle: About 20 cm. Fourth peduncle: About 18 cm. Seventh peduncle: About 9 cm. Diameter: About 6 mm. Strength: Strong. Aspect: Erect to about 10° from vertical. Texture: Smooth, glabrous. Color: 187A.

*Reproductive organs.*—Androecium: Quantity per disc floret: Five. Anther shape: Linear. Anther length: About 3 mm. Anther color: 17B. Pollen amount: Scarce. Pollen color: 17A. Gynoecium: Quantity per ray or disc floret: One. Pistil length: About 6 mm. Stigma shape: Lanceolate. Stigma color: 13A. Style length: About 2 mm. Style color: 1C. Ovary color: 9C. Seeds: Seed development has not been observed.

Disease/pest resistance: Plants of the new *Dahlia* have not been shown to be resistant to pathogens and pests common to *Dahlia*.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'Melody Harmony' as illustrated and described.

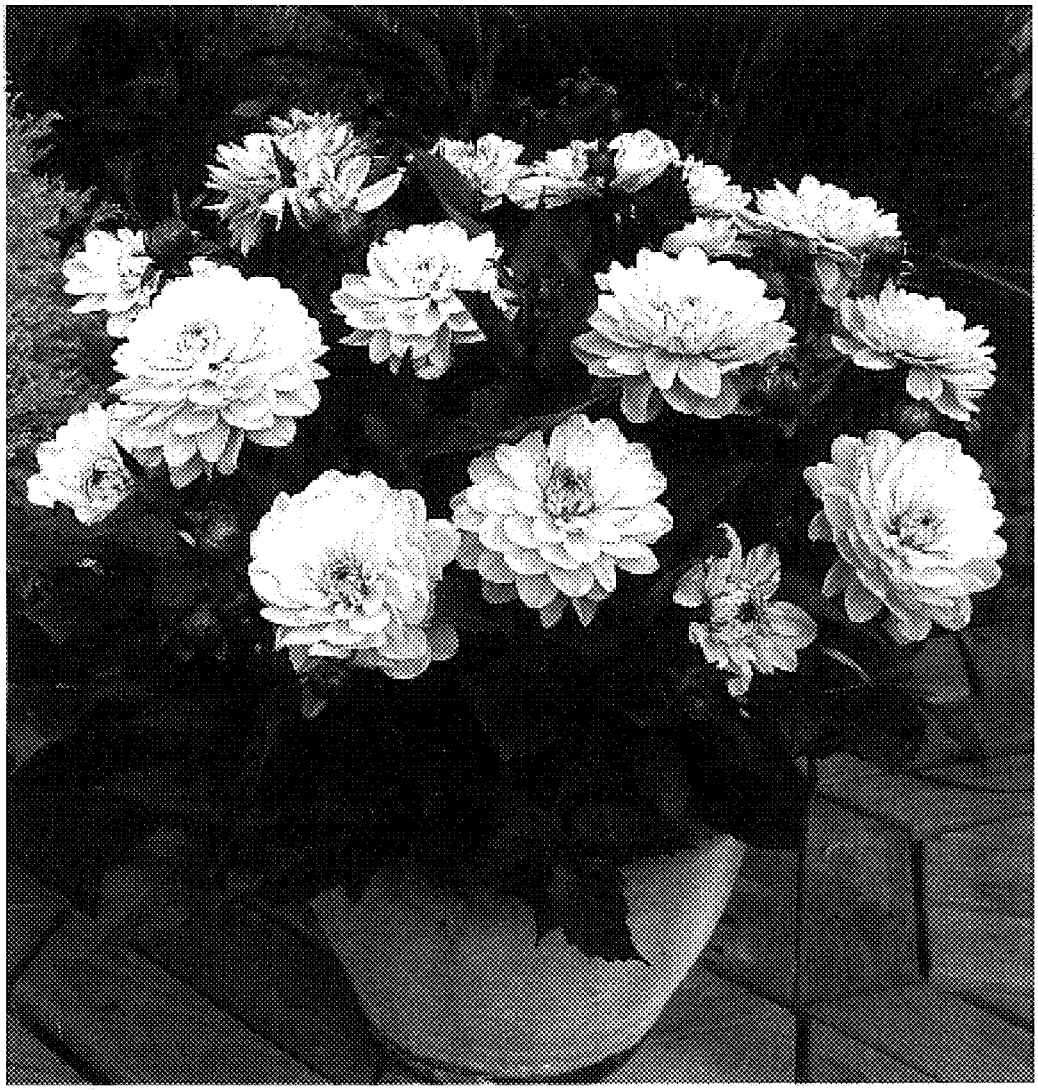

* * * * *